(12) United States Patent
Teng et al.

(10) Patent No.: US 7,166,293 B2
(45) Date of Patent: Jan. 23, 2007

(54) ANGIOGENESIS INHIBITORS

(75) Inventors: Che-Ming Teng, Taipei (TW);
Sheng-Chu Kuo, Taichung (TW); Fang Yu Lee, Tachia Taichung (TW);
Shiow-Lin Pan, Taipei (TW); Jih-Hwa Guh, Taipei (TW)

(73) Assignee: Carlsbad Technology, Inc., Carlsbad, CA (US)

( * ) Notice: Subject to any disclaimer, the term of this patent is extended or adjusted under 35 U.S.C. 154(b) by 0 days.

(21) Appl. No.: 10/147,445

(22) Filed: May 16, 2002

(65) Prior Publication Data

US 2003/0186996 A1 Oct. 2, 2003

Related U.S. Application Data

(60) Provisional application No. 60/368,892, filed on Mar. 29, 2002.

(51) Int. Cl.
*A01N 25/00* (2006.01)
*A01N 25/32* (2006.01)

(52) U.S. Cl. ..................... 424/405; 424/406
(58) Field of Classification Search ............ 514/405, 514/406
See application file for complete search history.

(56) References Cited

U.S. PATENT DOCUMENTS

| 5,574,168 | A | * | 11/1996 | Kuo et al. ............... 548/360.5 |
| 6,162,819 | A | * | 12/2000 | Schindler et al. ........... 514/405 |
| 6,284,763 | B1 | * | 9/2001 | Adams et al. .............. 514/248 |
| 6,458,797 | B1 | * | 10/2002 | Adams et al. ......... 514/252.16 |
| 2002/0103454 | A1 | * | 8/2002 | Sackner et al. ............... 604/19 |
| 2003/0171403 | A1 | * | 9/2003 | Garthwaite et al. ......... 514/326 |
| 2003/0186996 | A1 | | 10/2003 | Teng et al. |
| 2005/0119278 | A1 | | 6/2005 | Teng et al. |

FOREIGN PATENT DOCUMENTS

| JP | 2002-080367 | * | 3/2002 | |
| KR | 2001-0099431 | | 11/2001 | .............. 31/416 |
| WO | WO-01/2369 | | 1/2001 | |
| WO | WO-01/53268 | | 7/2001 | |
| WO | WO 01/54680 | | 8/2001 | |
| WO | WO 01/54771 | | 8/2001 | |
| WO | WO-02/10137 | | 2/2002 | |
| WO | WO-2005/030121 | | 4/2005 | |

OTHER PUBLICATIONS

Tulis et al., YC-1, a benzyl indazole derivative, stimulates vascular cGMP . . . , Database CAPLUS, AN2000:884445, abstract, Biochemical and Biophysical Research Communications, 2000, vol. 279(2), pp. 646-652.*
Becker et al., The vasodilator-stimulated phophoprotein . . . , Database CAPLUS AN2000:158699, abstract, Journal of Cadiovascular Pharmacology, 2000, vol. 35(3), pp. 390-397.*

S. L. Pan, et al. *Investigation of YC-1-Mediated Anti-Angiogenic Activity.* 17th Joint Annual Conference of Biomedical Sciences, Taipei, Taiwan. Mar. 23-24, 2002.
Database CAPLUS, Institute of Cardiavascular and Arteriosclerosis Research, (Wuppertal, Germany), AN2000:158699, Becker et al., The vasodilator-stimulated phosphoprotein(VASP): target of YC-1 and nitric oxide effects in human and rat platelets, abstract only, Journal of Cardiovascular Pharmacology, 2000, vol. 35, (3), pp. 390-397.
Chun et al., "Inhibitory Effect of YC-1 on the Hypoxic Induction of Erythropoietin and Vascular Endothelial Growth Factor in Hep3B Cells", Biochemical Pharmacology 61:947-964, 2001.
First Amended Complaint filed Nov. 8, 2005, in the U.S. District Court, Central District of California (Western Division—Los Angeles), Case No. 2.05-cv-07976-DDP-MAN, entitled "*HIF Bio Inc et al v. Yung Shin Pharmaceuticals Industrial Co Ltd et al*", (101 pages).
U.S. District Court, Central District of California (Western Division—Los Angeles), Civil Docket Sheet for Case No. 2:05-cv-07976-DDP-MAN, entitled "*HIF Bio Inc et al v. Yung Shin Pharmaceuticals Industrial Co Ltd et al*", filed Nov. 8, 2005 (9 pages).
European Search Report dated Feb. 3, 2006, Application No. 05291767.1-2123; France (8 pages).
Notification of the First Office Action, issued Jan. 20, 2006, during the prosecution of Chinese Application No. 03807442.7 (with English translation) (7 pages).

* cited by examiner

*Primary Examiner*—Vickie Kim
(74) *Attorney, Agent, or Firm*—Osha Liang LLP

(57) ABSTRACT

A method for treating an angiogenesis-related disorder. The method includes administrating to a subject in need thereof an effective amount of a compound of the formula:

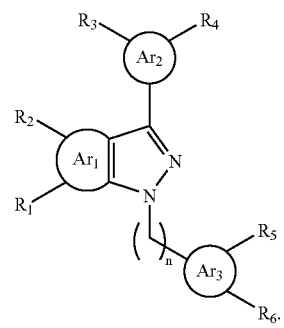

Each of $Ar_1$, $Ar_2$, and $Ar_3$, independently, is phenyl, thienyl, furyl, pyrrolyl, pyridinyl, or pyrimidinyl; each of $R_1$, $R_2$, $R_3$, $R_4$, $R_5$, and $R_6$, independently, is R, nitro, halogen, C(O)OR, C(O)SR, C(O)NRR', $(CH_2)_m$OR, $(CH_2)_m$SR, $(CH_2)_m$NRR', $(CH_2)_m$CN, $(CH_2)_m$C(O)OR, $(CH_2)_m$CHO, $(CH_2)_m$CH=NOR, or $R_1$ and $R_2$ together, $R_3$ and $R_4$ together, or $R_5$ and $R_6$ together are $O(CH_2)_m$O, in which each of R and R', independently, is H or $C_1$~$C_6$ alkyl; and m is 0, 1, 2, 3, 4, 5, or 6, and n is 0, 1, 2, or 3.

7 Claims, 2 Drawing Sheets

Compound 1 (mg/Kg/day)

ANGIOGENESIS INHIBITORS

RELATED APPLICATIONS

This application claims priority to U.S. provisional application No. 60/368,892, filed on Mar. 29, 2002, the content of which is incorporated herein by reference.

BACKGROUND

Angiogenesis, formation of new blood vessels, occurs in the healthy body for healing wounds and restoring blood flow to tissues after injury. The angiogenic process is tightly controlled by various positive and negative regulatory factors. In many disease states, the body loses control over angiogenesis.

Excessive blood vessel growth may be triggered by certain pathological conditions such as cancer, age-related macular degeneration, rheumatoid arthritis, and psoriasis. As a result of excessive angiogenesis, new blood vessels feed diseased tissues and destroy normal tissues. In cancer, the new vessels allow tumor cells to escape into the circulation and lodge in other organs.

Angiogenesis occurs via a series of sequential steps, including division and migration of endothelial cells that form the walls of blood vessels. About 15 proteins are known to activate endothelial cell growth and movement. Therefore, angiogenesis can be suppressed by inhibitors of these activating proteins, e.g., angiogenin, epidermal growth factor, estrogen, fibroblast growth factor, interleukin 8, prostaglandins E1 and E2, tumor necrosis factor, vascular endothelial growth factor, or granulocyte colony-stimulating factor.

Excessive angiogenesis-related disorders include cancer (both solid and hematologic tumors), cardiovascular diseases (e.g., atherosclerosis), chronic inflammation (e.g., rheutatoid arthritis or Crohn's disease), diabetes (e.g., diabetic retinopathy), psoriasis, endometriosis, and adiposity. See, e.g., Pharmacological Reviews 52: 237–268, 2001. Compounds that effectively inhibit angiogenesis are drug candidates for treating or preventing these disorders.

SUMMARY

This invention relates to methods of inhibiting angiogenesis with fused pyrazolyl compounds.

In one aspect, this invention features a method for treating an angiogenesis-related disorder (e.g., cardiovascular disease, chronic inflammation, diabete, psoriasis, endometriosis, or adiposity). The method includes administrating to a subject in need thereof an effective amount of a compound of the formula:

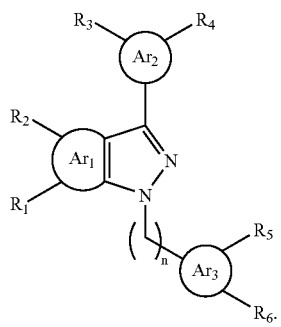

Each of $Ar_1$, $Ar_2$, and $Ar_3$, independently, is phenyl, thienyl, furyl, pyrrolyl, pyridinyl, or pyrimidinyl; each of $R_1$, $R_2$, $R_3$, $R_4$, $R_5$, and $R_6$, independently, is R, nitro, halogen, C(O)OR, C(O)SR, C(O)NRR', $(CH_2)_m OR$, $(CH_2)_m SR$, $(CH_2)_m NRR'$, $(CH_2)_m CN$, $(CH_2)_m C(O)OR$, $(CH_2)_m CHO$, $(CH_2)_m CH=NOR$, or $R_1$ and $R_2$ together, $R_3$ and $R_4$ together, or $R_5$ and $R_6$ together are $O(CH_2)_m O$, in which each of R and R', independently, is H or $C_1 \sim C_6$ alkyl; and m is 0, 1, 2, 3, 4, 5, or 6, and n is 0, 1, 2, or 3. $(CH_2)_m$ can be branched or linear. Note that the left atom shown in any substituted group described above is closest to the fused pyrazolyl ring. Also note that when there are one or more R or $(CH_2)_m$ moieties in a fused pyrazolyl compound, the R or the $(CH_2)_m$ moieties can be the same or different.

A subset of the above-described compounds are those in which each of $Ar_1$, $Ar_2$, and $Ar_3$ is phenyl or furyl. Further, each of $R_1$, $R_2$, $R_5$, and $R_6$ is H, and n is 1, e.g., 1-benzyl-3-(5'-hydroxymethyl-2'-furyl)indazole (Compound 1).

The term "Ar," as used herein, refers to both aryl and heteroaryl groups. Aryl, e.g., phenyl, is a hydrocarbon ring system having at least one aromatic ring. Heteroaryl is a hydrocarbon ring system having at least one aromatic ring which contains at least one heteroatom such as O, N, or S. Examples of heteroaryl include, but are not limited to, thienyl, furyl, pyrrolyl, pyridinyl, and pyrimidinyl. An "Ar" may contain one, two, three, or more substituents on its ring. In addition to those assigned to $R_1$, $R_2$, $R_3$, $R_4$, $R_5$, and $R_6$ (see above), the substituents can also be nitro, $C_2 \sim C_6$ alkenyl, $C_2 \sim C_6$ alkynyl, aryl, heteroaryl, cyclyl, or heterocyclyl. Alkyl, alkenyl, alkynyl, alkoxy, aryl, heteroaryl, cyclyl, and heterocyclyl, as used herein, are optionally substituted with $C_1 \sim C_6$ alkyl, halogen, amino, hydroxyl, mercapto, cyano, or nitro. Note that the term "alkyl" refers to both linear alkyl and branched alkyl.

The fused pyrazolyl compounds described above include the compounds themselves, as well as their salts and their prodrugs, if applicable. Such salts, for example, can be formed by interaction between a negatively charged substituent (e.g., carboxylate) on a fused pyrazolyl compound and a cation. Suitable cations include, but are not limited to, sodium ion, potassium ion, magnesium ion, calcium ion, and an ammonium cation such as teteramethylammonium ion. Likewise, a positively charged substituent (e.g., amino) can form a salt with a negatively charged counterion. Suitable counterions include, but are not limited to, chloride, bromide, iodide, sulfate, nitrate, phosphate, or acetate. Examples of prodrugs include esters and other pharmaceutically acceptable derivatives, which, upon administration to a subject, are capable of providing the fused pyrazolyl compounds described above.

The above-described compounds can also be used to treat cancer (e.g., lung cancer). More specifically, one or more of the compounds are administered an effective amount to a subject suffering from cancer.

As used herein, "cancer" refers to cellular tumor. Cancer cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type, or stage of invasiveness. Examples of cancers include, but are not limited to, carcinoma and sarcoma such as leukemia, sarcomas, osteosarcoma, lymphomas, melanoma, ovarian cancer, skin cancer, testicular cancer, gastric cancer, pancreatic cancer, renal cancer, breast cancer, prostate colorectal cancer, cancer of head and neck, brain cancer, esophageal cancer, bladder cancer, adrenal cortical cancer, lung cancer, bronchus cancer, endometrial cancer, nasopharyngeal cancer, cervical or hepatic cancer, or cancer of unknown primary site.

Also within the scope of this invention are a composition containing one or more of the fused pyrazolyl compounds described above for use in treating the afore-mentioned diseases, and the use of such a composition for the manufacture of a medicament for the just-described treatment.

Other features, objects, and advantages of the invention will be apparent from the description and drawings, and from the claims.

DETAILED DESCRIPTION

Figure 1:
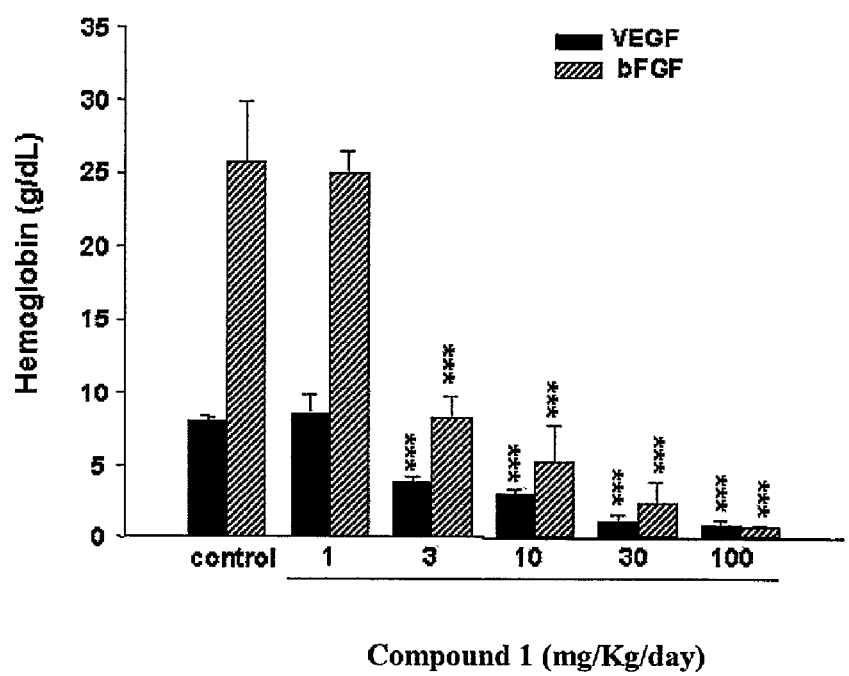
FIG. 1 shows the effect of Compound 1 on nude mice administered with a Matrigel plug containing 150 ng/mL vascular endothelial growth factor (VEGF) or basic fibroblast growth factor (bFGF).

A fused pyrazolyl compound used to practice the method of this invention can be prepared by procedures well known to a skilled person in the art (see, e.g., U.S. Pat. No. 5,574,168). They include the following synthetic route: An aryl aryl ketone is first prepared by coupling an arylcarbonyl chloride with another aryl compound. Either aryl compound is optionally mono- or multi-substituted. The ketone then reacts with an arylalkylhydrazine, the aryl group of which is also optionally mono- or multi-substituted, to form a hydrazone containing three aryl groups. The hydrazone group is transformed into a fused pyrazolyl core via an alkylene linker, another aryl group is fused at 4-C and 5-C of the pyrazolyl core, and the third aryl group is directly connected to 3-C of the pyrazolyl core. Derivatives of the fused pyrazolyl compound may be obtained by modifying the substituents on any of the aryl groups.

The chemicals used in the above-described synthetic route may include, for example, solvents, reagents, catalysts, protecting group and deprotecting group reagents. The methods described above may also additionally include steps, either before or after the steps described specifically herein, to add or remove suitable protecting groups in order to ultimately allow synthesis of the fused pyrazolyl compound. In addition, various synthetic steps may be performed in an alternate sequence or order to give the desired compounds. Synthetic chemistry transformations and protecting group methodologies (protection and deprotection) useful in synthesizing applicable fused pyrazolyl compounds are known in the art and include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A fused pyrazolyl compound thus synthesized can be further purified by a method such as column chromatography, high pressure liquid chromatography, or recrystallization.

This invention features a method for treating an angiogenesis-related disorder (e.g., cancer or an ocular disease). The method includes administering to a subject in need thereof an effective amount of one or more fused pyrazolyl compounds and a pharmaceutically acceptable carrier. The term "treating" is defined as the application or administration of a composition including the fused pyrazolyl compound to a subject, who has a angiogenesis-related disease, a symptom of such a disease, or a predisposition toward such a disease, with the purpose to cure, heal, alleviate, relieve, alter, remedy, ameliorate, improve, or affect the disease, the symptoms of the disease, or the predisposition toward the disease. "An effective amount" is defined as the amount of a fused pyrazolyl compound which, upon administration to a subject in need thereof, is required to confer therapeutic effect on the subject. An effective amount of a fused pyrazolyl compound may range from about 1 mg/Kg to about 100 mg/Kg. Effective doses also vary, as recognized by those skilled in the art, depending on route of administration, excipient usage, and the possibility of co-usage with other agents for treating an angiogenesis-related disorder.

To practice the method of the present invention, a fused pyrazolyl compound can be administered orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A composition for oral administration can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A carrier in a pharmaceutical composition must be "acceptable" in the sense of being compatible with the active ingredient of the formulation (and preferably, capable of stabilizing it) and not deleterious to the subject to be treated. For example, solubilizing agents, such as cyclodextrins (which form specific, more soluble complexes with fused pyrazolyl compounds), can be utilized as pharmaceutical excipients for delivery of fused pyrazolyl compounds. Examples of other carriers include colloidal silicon dioxide, magnesium stearate, cellulose, sodium lauryl sulfate, and D&C Yellow #10.

A suitable in vitro assay can be used to preliminarily evaluate the efficacy of a fused pyrazolyl compound in inhibiting the activities of fibroblast growth factor (FGF) or vascular endothelial growth factor (VEGF). In vivo assays can also be performed by following procedures well known in the art to screen for efficacious fused pyrazolyl compounds. See the specific examples below.

Without further elaboration, it is believed that the above description has adequately enabled the present invention. The following specific embodiments are, therefore, to be construed as merely illustrative, and not limitative of the remainder of the disclosure in any way whatsoever. All of the publications, including patents, cited herein are hereby incorporated by reference in their entirety.

Synthesis of 1-benzyl-3-(5'-hydroxymethyl-2'-furyl)indazole (Compound 1)

Calcium borohydride was first prepared by stirring anhydrous calcium chloride (88.8 mg, 0.8 mmole) with sodium borohydride (60 mg, 1.6 mmole) in anhydrous THF (20 mL) for 4 hrs. Then a 30 mL THF solution containing 88.0 mg 1-benzyl-3-(5'-methoxycarbonyl-2'-furyl)indazole (0.27 mmole) was added dropwise to the calcium borohydride solution at 30±2° C. The mixture was heated under reflux for 6 hrs, cooled, quenched into crushed ice, placed at a reduced pressure to remove THF, and filtered to obtain a solid product. The solid was extracted with dichloromethane. The extract was concentrated to 50 mL and a solid precipitated after petroleum ether was added. The precipitate was collected and purified by column chromatography (silica gel-benzene) to obtain 70.0 mg 1-benzyl-3-(5'-hydroxymethyl-2'-furyl)indazole at a yield of 87%.

mp: 108–109° C.

MS (%), m/z: 304 (M$^+$).

IR (KBr) $v_{max}$: 3350 cm$^{-1}$ (—OH).

$^1$H-NMR (DMSO-d$_6$, 200 MHz) δ: 4.51 (2H, d, J=5.5 Hz, —CH$_2$O—), 5.31 (1H, t, J=5.5 Hz, —OH), 5.70 (2H, s, =NCH$_2$—), 6.48 (1H, d, J=3.4 Hz, H-4'), 6.97 (1H, d, J=3.4 Hz, H-3'), 7.21–7.31 (6H, m, H-5, phenyl), 7.45 (1H, t, J=8.2 Hz, H-6), 7.75 (1H, dd, J=8.2, 1.8 Hz, H-7), 8.12 (1H, dd, J=8.2. 1.0 Hz. C4-H).

Inhibition of DNA Synthesis

Human umbilical vein endothelial cells (HUVECs) were incubated in the absence of Compound 1 (basal and control) or presence of Compound 1 (with a concentration of 0.1 µM, 0.03 µM, 0.1 µM, 0.3 µM, or 1 µM). Vascular endothelial growth factor (VEGF) or basic fibroblast growth factor (bFGF) was added (except for basal) to induce DNA synthesis, which was detected based on [$^3$H]thymidine incorporation. The results show that Compound 1 inhibited VEGF- and bFGF-induced cell proliferation of HUVECs in a concentration-dependent manner. Unexpectedly, Compound 1 has IC$_{50}$ values of 9.0×10$^{-8}$ M and 1.4×10$^{-7}$ M, for VEGF and bFGF, respectively.

Additional 23 fused pyrazolyl compounds were also tested. All of them inhibited VEGF-induced cell proliferation of HUVECs, some as potent as Compound 1.

Inhibition of Tube Formation

HUVECs were cultured onto chamberslide, which was pre-coated with Matrigel (10 mg/mL). Cells were treated without Compound 1 (control) or with Compound 1 (10 µM). VEGF (10 ng/mL) or bFGF (10 ng/mL) was added to induce tube formation. All photos were taken at 100× magnification. The results show that Compound 1 inhibited VEGF- and bFGF-induced formation of networks of elongated endothelial cells.

Inhibition of Angiogenic Effect

Nude mice were subcutaneously injected with a Matrigel plug containing 150 ng/mL VEGF or bFGF. Vehicle or Compound 1 was administered to the mice orally (1 mg/kg/day, 3 mg/kg/day, 10 mg/kg/day, 30 mg/kg/day, or 100 mg/kg/day) for seven days. The angiogenic response was monitored visually through the transparent skin. Matrigel itself did not elicit an angiogenic response. After seven days the mice were sacrificed and the Matrigel plugs were observed in situ to quantify the ingrowth of blood vessels. The plugs were removed, fixed in 4% formaldehyde, embedded in paraffin, sectioned at 5-µm thick for histological analysis, and blood vessel growth quantitated by hematoxylin-eosin staining. All photos were taken at 40× magnification. The results show that oral administration of Compound 1 for seven days effectively inhibited VEGF or bFGF-induced angiogenic effect in a dose-dependent manner.

In a quantitative analysis of angiogenic effect, nude mice were treated as described above, and the plugs were removed and dissolved. Hemoglobin concentrations were measured using a hemoglobin detection kit (Sigma Chem. Co.) as indices of angiogenesis. Means±S.E. (n=3) were presented (see FIG. 1). Symbol "***" represents P<0.001 that are compared with the control. The results illustrates that Compound 1 effectively inhibited VEGF or bFGF-induced angiogenic effect.

Anti-tumor Activity

Figure 2:
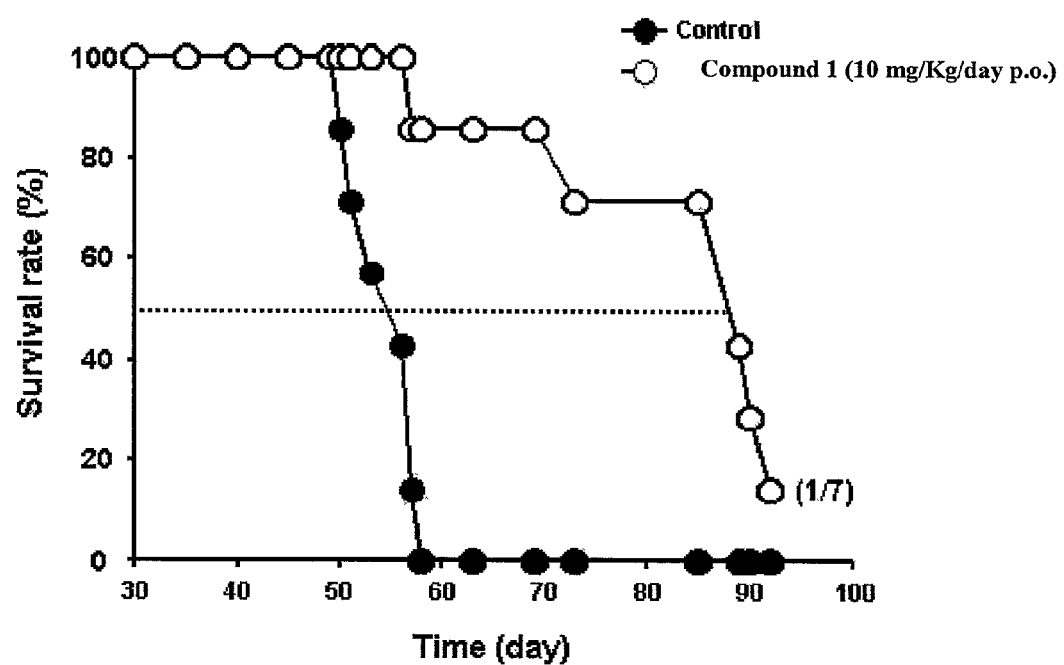
FIG. 2 shows the effect of Compound 1 on nude mice implanted with A549 lung tumor cells.

10$^6$ A549 lung tumor cells were introduced into the pleural space of nude mice. Compound 1 was administered to the mice orally (10 mg/kg/day). The survival rates of Compound 1-treated mice and control mice were compared (FIG. 2). The life span (i.e., the medium survival time) of Compound 1-treated mice was about 1.8 times that of control mice, as analyzed by a % T/C value [(median survival time of treatment/median survival time of control)× 100].

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, a compound structurally analogous to a fused pyrazolyl compound can also be used to practice the present invention. Thus, other embodiments are also within the claims.

What is claimed is:

1. A method for inhibiting endothelial cell proliferation, comprising administering to a subject in need thereof an effective amount of a compound of the formula:

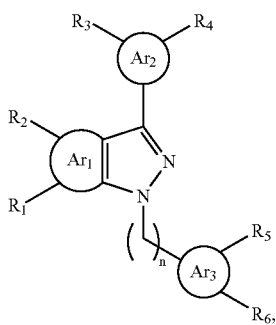

Wherein
each of $Ar_1$, and $Ar_3$ is phenyl;
$Ar_2$ is furyl or phenyl;
one of $R_1$, and $R_2$ is H, and the other is $C_1$–$C_6$ alkyl or halogen;
one of $R_3$, and $R_4$ is H, and the other is $CH_2OH$;
each of $R_5$, and $R_6$ is H;
n is 1; and
said endothelial cell proliferation is responsible for treating an angiogenesis-related disorder.

2. The method of claim 1, wherein $Ar_2$ is 5'-furyl.

3. The method of claim 2, wherein $R_3$ is substituted at position 2 of furyl.

4. The method of claim 3, wherein $R_3$ is $CH_2OH$ and $R_4$ is H.

5. The method of claim 4, wherein $R_1$ and $R_2$ are substituted at positions 4 and 5 of phenyl.

6. The method of claim 5, wherein $R_1$ is H, and $R_2$ is $CH_3$.

7. The method of claim 6, wherein $R_1$ is H, and $R_2$ is F.

* * * * *